US009650398B2

United States Patent
Fujimoto et al.

(10) Patent No.: US 9,650,398 B2
(45) Date of Patent: May 16, 2017

(54) LECITHIN OR LECITHIN PREPARATION HAVING RESISTANCE TO HEAT DISCOLORATION AND A METHOD FOR PRODUCING THE SAME

(71) Applicant: Tsuji Oil Mills Co., Ltd., Mie (JP)

(72) Inventors: Yuki Fujimoto, Mie (JP); Akihito Hayashi, Mie (JP); Nobutoshi Hamaguchi, Mie (JP)

(73) Assignee: Tsuji Oil Mills Co., Ltd., Matsusaka (JP)

( * ) Notice: Subject to any disclaimer, the term of this patent is extended or adjusted under 35 U.S.C. 154(b) by 0 days.

(21) Appl. No.: 14/574,958

(22) Filed: Dec. 18, 2014

(65) Prior Publication Data

US 2015/0181905 A1    Jul. 2, 2015

(30) Foreign Application Priority Data

Dec. 27, 2013   (JP) .................. 2013-272380

(51) Int. Cl.

| | |
|---|---|
| *C07F 9/10* | (2006.01) |
| *A23D 9/04* | (2006.01) |
| *C11B 3/10* | (2006.01) |
| *A23L 5/20* | (2016.01) |
| *A23J 7/00* | (2006.01) |
| *A23K 10/30* | (2016.01) |
| *C11B 3/00* | (2006.01) |
| *A61K 31/685* | (2006.01) |

(52) U.S. Cl.
CPC ............. *C07F 9/103* (2013.01); *A23D 9/04* (2013.01); *A23L 5/273* (2016.08); *C11B 3/10* (2013.01); *A23J 7/00* (2013.01); *A23K 10/30* (2016.05); *A61K 31/685* (2013.01); *C11B 3/008* (2013.01)

(58) Field of Classification Search
None
See application file for complete search history.

(56) References Cited

U.S. PATENT DOCUMENTS 4,524,085 A * 6/1985 Purves ................. A23D 9/013
426/601
2005/0003065 A1   1/2005 Liu

FOREIGN PATENT DOCUMENTS

| | | |
|---|---|---|
| EP | 1 137 650 A1 | 10/2001 |
| GB | 2 149 811 A | 6/1985 |

(Continued)

OTHER PUBLICATIONS

JPS 54-127907, Hohnen Oil Co. LTD., Preparation of oil for roasting on hot plates, 1979, English translation, 7 pages.*

(Continued)

*Primary Examiner* — Yate K Cutliff
(74) *Attorney, Agent, or Firm* — Mintz Levin Cohn Ferris Glovsky and Popeo, P.C.; David G. Conlin; Joohee Lee

(57) ABSTRACT

To provide a lecithin or lecithin preparation of which resistance to heat discoloration is achieved without significant change of the phospholipid composition of the lecithin nor of the oligosaccharide content; and a method for producing the same. A lecithin or lecithin preparation obtained by bringing a lecithin into contact with an adsorbent and removing the adsorbent, the lecithin or lecithin preparation having resistance to heat discoloration and having an oligosaccharide content being 50% by mass or more of the content before the contact with the adsorbent.

12 Claims, 2 Drawing Sheets

(56) References Cited

FOREIGN PATENT DOCUMENTS

| JP | 54-112825 | | 9/1979 | | |
|----|-----------|---|--------|---|---|
| JP | 54-124009 | | 9/1979 | | |
| JP | S 54-127907 | * | 10/1979 | ............... | A23D 5/02 |
| JP | 05-227897 | | 9/1993 | | |
| JP | 2007-68462 | | 3/2007 | | |
| WO | 00/34292 A1 | | 6/2000 | | |

OTHER PUBLICATIONS

JP54-124009, Honen Oil Co. LTD, Suppression of heat browning of phospholiids, 1979, English translation, 5 pages.*

JP54-112825, Hohnen Oil Co. LTD, Prevention of heat browning of phospholipids, 1979, English translation, 5 pages.*

European Search Report in corresponding European Patent Application No. 14199655.3, mailed Apr. 28, 2015.

H.E. Helmy et al., "Treatments of phospholipids to prevent or decrease colour fixation in cottonseed oil", Die Nahrung, 38(4), pp. 418-426 (1994).

* cited by examiner

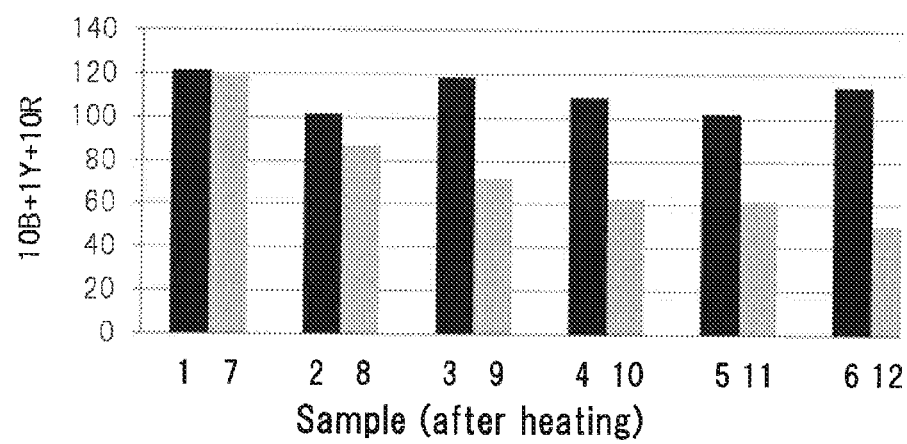
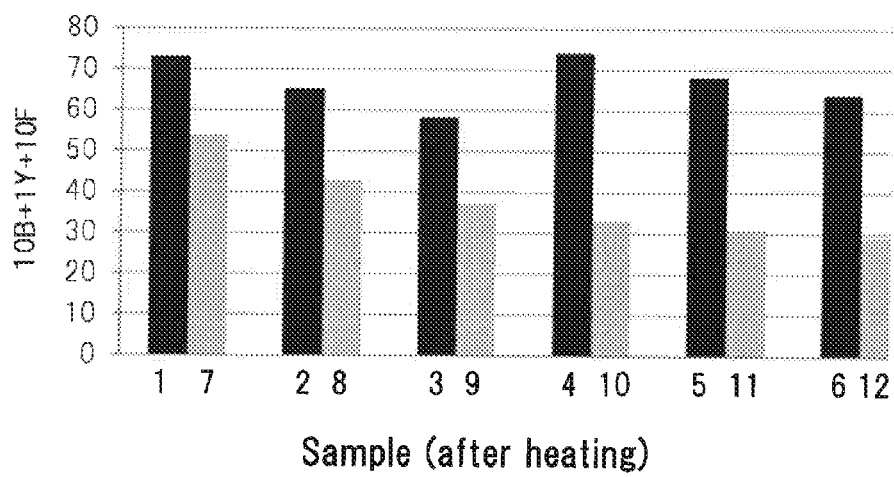

LECITHIN OR LECITHIN PREPARATION HAVING RESISTANCE TO HEAT DISCOLORATION AND A METHOD FOR PRODUCING THE SAME

TECHNICAL FIELD

The present invention relates to a lecithin or lecithin preparation having resistance to heat discoloration and a method for producing the same.

BACKGROUND ART

Lecithin is a generic name for a mixture mainly comprising various phospholipids, and the major components thereof are phosphatidylcholine (PC), phosphatidylethanolamine (PE), phosphatidylinositol (PI), phosphatidylserine (PS), phosphatidylglycerol (PG), phosphatidic acid (PA), and acyl glycero phospholipids including lysophospholipids derived from these phospholipids by hydrolysis of a fatty acid at the sn-1 or the sn-2 position. Lecithin is broadly present in living organisms such as animals, plants, and microorganisms, and is particularly contained much in brains and livers of animals, egg yolks, soybeans, yeasts, and the like. Lecithin is broadly used as a natural emulsifier for foods, industrial products, cosmetics, medicines, and the like. Since lecithin is excellent in preventive effect on oil splattering caused by other ingredients and mold release effect, known examples of edible oils and fats for which lecithin is used include a stir-frying oil, a mold release oil, a fried rice oil, a frying oil, and the like, which are edible oils and fats prepared by addition and dissolution of lecithin. However, when lecithin-containing oil or fat is heated (at a temperature of 120° C. or more), the oil or fat gradually turns brownish yellow, brown, and almost black in the end. Accordingly, when a lecithin-containing oil or fat is used for a stir-frying oil for example, discoloration by heating occurs, leading to problems such as bad appearance of stir-fried dishes.

As a method for suppressing the heat discoloration of lecithin, a method in which an additive for suppressing the discoloration is used has been developed. For example, Patent Literature 1 discloses a method for suppressing the heat discoloration of a lecithin-containing oil or fat, in which polyglycerin-condensed ricinoleic acid ester is added thereto. Moreover, a method in which lecithin is modified has been also developed as a method for suppressing the heat discoloration of lecithin. The causative substances of the heat discoloration of lecithin are phosphatidylethanolamine or α-galacto-oligosaccharides such as raffinose and stachyose, which are involved in the amino-carbonyl reaction considered to be a major cause of heat discoloration. Based on the fact, Patent Literature 2, for example, discloses a lecithin having resistance to heat discoloration obtained by adding a small amount of activated clay or an adsorbent such as silica gel to an alcohol solution of a lecithin, followed by mixing with stirring, removing the adsorbent by filtration, and distilling off the solvent; and a lecithin having resistance to heat discoloration obtained by passing a hydroalcoholic solution of lecithin through a non-polar styrene-vinylbenzene based synthetic resin adsorbent to wash α-galacto-oligosaccharides with hydrous alcohol, eluting lecithin with absolute alcohol, and distilling off the solvent.

CITATION LIST

Patent Literature

PTL 1: JP 2007-68462 A
PTL 2: JP H5-227897 A

SUMMARY OF INVENTION

Technical Problem

An objective of the present invention is to provide a lecithin or lecithin preparation of which resistance to heat discoloration is achieved without significant change of the phospholipid composition of the lecithin nor of the oligosaccharide content; and a method for producing the same.

Solution to Problem

In order to solve the problem, the present invention encompasses the inventions below.

[1] A lecithin or lecithin preparation obtained by bringing a lecithin into contact with an adsorbent and removing the adsorbent, the lecithin or lecithin preparation having resistance to heat discoloration and having an oligosaccharide content being 50% by mass or more of the content before the contact with the adsorbent.

[2] The lecithin or lecithin preparation according to the above [1], having a phosphatidylethanolamine content being 80% by mass or more of the content before the contact with the adsorbent.

[3] The lecithin or lecithin preparation according to the above [1] or [2], wherein the adsorbent is one or more selected from the group consisting of a metal silicate, a metal oxide, an activated carbon, a zeolite, an activated clay, and a silica gel.

[4] The lecithin or lecithin preparation according to the above [3], wherein the adsorbent is one or more metal silicates selected from the group consisting of magnesium silicate, calcium silicate, aluminum silicate, sodium silicate, potassium silicate, calcium aluminosilicate, calcium magnesium silicate, and sodium aluminosilicate.

[5] A method for producing a lecithin or lecithin preparation having resistance to heat discoloration, comprising:
   step 1: dissolving a lecithin in a solvent or dispersing a lecithin in a dispersion medium to prepare a lecithin solution or a lecithin dispersion;
   step 2: bringing the obtained lecithin solution or lecithin dispersion into contact with an adsorbent; and
   step 3: removing the adsorbent from the lecithin solution or the lecithin dispersion.

[6] The production method according to the above [5], wherein the lecithin dispersion is prepared using an oil or fat as the dispersion medium in the step 1.

[7] The production method according to the above [5] or [6], comprising adjusting the acid value of the lecithin solution or the lecithin dispersion in the step 1.

[8] The production method according to any one of the above [5] to [7], wherein the adsorbent is one or more selected from the group consisting of a metal silicate, a metal oxide, an activated carbon, a zeolite, an activated clay, and a silica gel.

[9] The production method according to the above [8], wherein the adsorbent is one or more metal silicates selected from the group consisting of magnesium silicate, calcium silicate, aluminum silicate, sodium silicate, potassium silicate, calcium aluminosilicate, calcium magnesium silicate, and sodium aluminosilicate.

[10] An edible oil or fat comprising the lecithin or lecithin preparation according to any one of the above [1] to [4].

[11] A food additive comprising the lecithin or lecithin preparation according to any one of the above [1] to [4].

[12] A cosmetic comprising the lecithin or lecithin preparation according to any one of the above [1] to [4].

[13] A medicine comprising the lecithin or lecithin preparation according to any one of the above [1] to [4].

[14] A feed comprising the lecithin or lecithin preparation according to any one of the above [1] to [4].

[15] An industrial product comprising the lecithin or lecithin preparation according to any one of the above [1] to [4].

[16] A food or drink comprising the edible oil or fat according to the above [10] and/or the food additive according to the above [11].

[17] A method for suppressing heat discoloration of a lecithin or lecithin preparation, comprising using the lecithin or lecithin preparation according to any one of the above [1] to [4].

[18] A method for suppressing heat discoloration of a lecithin-containing edible oil or fat, comprising adding the lecithin or lecithin preparation according to any one of the above [1] to [4] to the edible oil or fat.

Advantageous Effects of Invention

The present invention can provide a lecithin or lecithin preparation having resistance to heat discoloration, and a method for producing the same. Since neither the phospholipid composition nor the oligosaccharide content of the lecithin or lecithin preparation of the present invention is significantly changed from those of the raw-material lecithin, heat discoloration can be suppressed without impairing the original functions of lecithin. Moreover, the present invention enables the production of a lecithin or lecithin preparation having resistance to heat discoloration at low cost. The use of an edible oil or fat containing the lecithin or lecithin preparation of the present invention, for example, as a stir-frying oil, a mold release oil, a frying oil, or the like can provide a high-quality processed food having suppressed heat discoloration of lecithin.

BRIEF DESCRIPTION OF DRAWINGS

FIG. 1 shows the examination results of the suppressing effect of magnesium silicate treatment on discoloration of soybean lecithin paste (trade name: SLP-PASTE, manufactured by Tsuji Oil Mills Co., Ltd.).

FIG. 2 shows the examination results of the suppressing effect of magnesium silicate treatment on discoloration of fractionated lecithin paste (trade name: SLP-PC35, manufactured by Tsuji Oil Mills Co., Ltd.).

DESCRIPTION OF EMBODIMENTS

Figure 3:
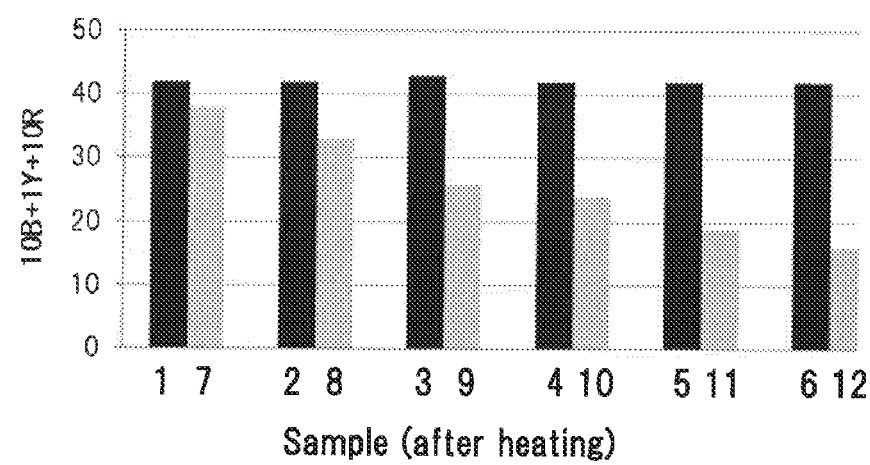
FIG. 3 shows the examination results of the suppressing effect of magnesium silicate treatment on discoloration of fractionated lecithin lump (trade name: SLP-PC70, manufactured by Tsuji Oil Mills Co., Ltd.).

The present invention provides a lecithin or lecithin preparation having resistance to heat discoloration. Lecithin is a generic name for a mixture mainly comprising various phospholipids. Examples of the phospholipid which is a major component of lecithin include phosphatidylcholine (PC), phosphatidylethanolamine (PE), phosphatidylinositol (PI), phosphatidylserine (PS), phosphatidylglycerol (PG), phosphatidic acid (PA), and acyl glycero phospholipids including lysophospholipids derived from these phospholipids by hydrolysis of a fatty acid at the sn-1 or the sn-2 position. A single component selected from the above phospholipids or a mixture of two or more kinds thereof may be referred to as lecithin. For industrial purposes, mixtures with a phospholipid purity of 60% by mass or more are used as lecithin. The phospholipid purity can be calculated by subtracting the weight of toluene-insoluble matter and acetone-soluble matter from the weight of a mixture, taking advantage of the property that a phospholipid is dissolved in toluene easily and not in acetone. Lecithin includes a fractionated lecithin, which is obtained by subjecting a lecithin to solvent fractionation; an enzyme-degraded lecithin or an enzyme-treated lecithin, which is obtained by subjecting a lecithin to enzyme treatment; a hydrogenated lecithin, which is obtained by subjecting a lecithin to hydrogenation; an acetylated lecithin, which is obtained by subjecting a lecithin to acetylation; a hydroxylated lecithin, which is obtained by subjecting a lecithin to hydroxylation; and a lecithin obtained by a combination of solvent fractionation, enzyme treatment, hydrogenation, acetylation, and/or hydroxylation. The form of the lecithin is not particularly limited, and may be any form such as a powder, a paste, or a lump.

Lecithin preparation is a generic name for a mixture of a lecithin as a main active ingredient and an auxiliary agent added for convenience in use. Examples of the auxiliary agent include food additives such as a manufacturing agent, an enzyme, a pH adjuster, a preservative, a sterilizer, an antioxidant, an antifungal agent, a shelf life improver, a colorant, a color improver, a decolorant, a brightener, a flavor, a spice extract, a sweetener, an acidulant, a seasoning, a bittering agent, an emulsifier, a thickener, a stabilizer, a gelatinizer, an adhesive paste, a leavening agent, a gum base, a yeast food, a softener, and an enrichment; food materials such as a lipid, a carbohydrate, a processed starch, a protein, and a peptide; and water. The auxiliary agents may be used alone or in combination of two or more kinds thereof. The form of the lecithin preparation is not particularly limited, and may be any form such as a powder, a paste, and a lump.

The source material of the lecithin is not particularly limited, and preferred examples thereof include, plants, animals, and aquatic animals and plants. Specific examples of the lecithin derived from a plant include lecithins obtained from a by-product (for example, a hydrate generated in the degumming process) of the purification of a vegetable oil of tung, linseed, almond, inca inchi, perilla, olive, orange seed, pumpkin seed, kapok, mustard, *Trichosanthes kirilowii* seed, *Catalpa ovata* seed, *Calendula officinalis* seed, wheat germ, rice bran, corn, sesame, cherry seed, safflower, pomegranate seed, *Perilla frutescens*, snakeguard seed, soybean, tea seed, evening primrose seed, camellia, rapeseed, *Momordica charantia* seed, *Campsis grandiflora* seed, balsam apple seed, palm, sunflower, peanut, grape seed, *Impatiens balsamina* seed, macadamia nut, cottonseed, and ground nut. Specific examples of the lecithin derived from an animal include egg-yolk lecithin. Specific examples of the lecithin derived from an aquatic animal include lecithins obtained from sardine, salmon, mackerel, saury, herring, tuna, squid, Alaska Pollack, bonito, seal, krill, sand eel, and salmon roe.

The lecithin or lecithin preparation of the present invention having resistance to heat discoloration (hereinafter referred to as "the lecithin of the present invention") is obtained by bringing a lecithin into contact with an adsorbent and removing the adsorbent. The lecithin of the present invention is preferably produced by a method comprising:

step 1: dissolving a lecithin in a solvent or dispersing a lecithin in a dispersion medium to prepare a lecithin solution or a lecithin dispersion;

step 2: bringing the obtained lecithin solution or lecithin dispersion into contact with an adsorbent; and step 3: removing the adsorbent from the lecithin solution or the lecithin dispersion (hereinafter referred to as "the production method of the present invention").

The method may comprise a different step in addition to the steps 1 to 3 as long as the lecithin of the present invention can be produced, and the step is not particularly limited. For example, the method may comprise, after the step 3, the step of concentrating and/or drying the lecithin solution or the lecithin dispersion from which the adsorbent has been removed. The phospholipid purity can be adjusted as appropriate in the step, and a lecithin from which the solvent or the dispersion medium has been removed can be obtained.

The step 1 is a step of dissolving a lecithin in a solvent or dispersing a lecithin in a dispersion medium to prepare a lecithin solution or a lecithin dispersion. The preparation of the lecithin solution or the lecithin dispersion enables the lecithin to contact with an adsorbent easily and efficiently.

The solvent used for dissolving the lecithin may be any solvent which can dissolve lecithin. Examples thereof include organic solvents such as a carboxylic acid alkyl ester, an alkane, an aliphatic hydrocarbon, an alicyclic hydrocarbon, an aromatic hydrocarbon, a halogenated hydrocarbon, and an alcohol. These solvents may be used alone or in combination of two or more kinds thereof. Specific examples thereof include methyl acetate, ethyl acetate, methyl propionate, methyl butyrate, methyl valerate, methyl caproate, hexane, heptane, octane, nonane, decane, liquid paraffin, petroleum ether, cyclohexane, methylcyclohexane, cyclooctane, benzene, toluene, xylene, methylene chloride, dichloromethane, chloroform, carbon tetrachloride, methanol, ethanol, and isopropyl alcohol.

The dispersion medium used for dispersing the lecithin may be any dispersion medium which can disperse lecithin, and examples thereof include oils and fats derived from plants, animals, aquatic animals and plants, and microorganisms. These dispersion media may be used alone or in combination of two or more kinds thereof. Specific examples of the oil or fat derived from a plant include lung oil, linseed oil, almond oil, inca inchi oil, perilla oil, olive oil, orange seed oil, pumpkin seed oil, kapok oil, mustard oil, *Trichosanthes kirilowii* seed oil, *Catalpa ovata* seed oil, a conjugated linoleic acid-containing oil or fat, *Calendula officinalis* seed oil, wheat germ oil, rice bran oil, corn oil, sesame oil, cherry seed oil, safflower oil, pomegranate seed oil, *Perilla frutescens* oil, snakeguard seed oil, soybean oil, tea seed oil, evening primrose seed oil, camellia oil, rapeseed oil, *Momordica charantia* seed oil, *Campsis grandiflora* seed oil, balsam apple seed oil, palm oil, sunflower oil, peanut oil, grape seed oil, *Impatiens balsamina* seed oil, macadamia nut oil, cottonseed oil, and ground nut oil. Specific examples of the oil or fat derived from an animal include beef tallow, lard, and egg yolk oil. Specific examples of the oil or fat derived from an aquatic animal include fish body oils obtained from sardine, salmon, mackerel, saury, herring, tuna, and other fishes, liver oils of squid and Alaska Pollack, orbital oils of bonito, tuna, and the like, seal oil, and krill oil. Specific examples of the oil or fat derived from a microorganism include an oil derived from *Schizochytrium* sp., an oil derived from *Nitzschia* sp., an oil derived from *Nannochloris* sp., and an oil derived from *Mortierella* sp.

Among the above solvents and dispersion media, oils and fats are preferred for use as a dispersion medium. The use of such an oil or fat can provide a lecithin-containing oil or fat without any further step of, for example, separating lecithin after the removal of the adsorbent in the step 3. Accordingly the lecithin-containing oil or fat having resistance to heat discoloration can be produced in fewer steps, and the cost can be reduced.

The lecithin content in the lecithin solution or the lecithin dispersion prepared in the step 1 is not particularly limited, and the total phospholipid content may be preferably about 0.1 to 90% by mass, more preferably about 10 to 60% by mass, and still more preferably about 15 to 30% by mass. The method for measuring the total phospholipid content is not particularly limited, and an appropriately selected publicly known method for measuring phosphorus may be used. For example, the total phospholipid content can be measured in accordance with "Standard Methods for the Analysis of Fats, Oils and Related Materials, 4.3.3.1-1996, Phospholipid Composition (Thin-Layer Chromatography)".

In the production method of the present invention, the acid value of the lecithin solution or the lecithin dispersion is preferably adjusted in the step 1. Although the reason is unclear, the inventors have confirmed that the higher the acid value of the lecithin solution or the lecithin dispersion before the adsorbent treatment is, the higher the resistance to heat discoloration after the adsorbent treatment is. The acid value of the lecithin solution or the lecithin dispersion is preferably adjusted according to the total phospholipid content in the solution or the dispersion. For example, when the total phospholipid content in the lecithin solution or the lecithin dispersion is 25% by mass, the acid value is preferably 10 or more, more preferably about 15 or more, even more preferably about 20 or more, still more preferably about 25 or more, even more preferably about 30 or more, and still more preferably about 35 or more. When the total phospholipid content in the solution or the dispersion is 50% by mass, the acid value is preferably about 20 or more, and more preferably about 30 or more, even more preferably about 40 or more, still more preferably about 50 or more, even more preferably about 60 or more, and still more preferably about 70 or more. When the total phospholipid content in the solution or the dispersion is 2.5% by mass, the acid value is preferably about 1 or more, and more preferably about 1.5 or more, even more preferably about 2 or more, still more preferably about 2.5 or more, even more preferably about 3 or more, and still more preferably about 3.5 or more. Even when the total phospholipid content in the solution or the dispersion is other than the above, the acid value can be adjusted in a similar manner.

The adjustment of the acid value of the lecithin solution or the lecithin dispersion is preferably performed by addition of an acid to the solution or the dispersion. The acid to be added may be any acid which can adjust the acid value of the lecithin, and examples thereof include inorganic acids, organic acids, and free fatty acids. These acids may be used alone or in combination of two or more kinds thereof. Specific examples of the inorganic acid include hydrochloric acid, nitric acid, sulfuric acid, phosphoric acid, boric acid, and hydrofluoric acid. Specific examples of the organic acid include formic acid, acetic acid, citric acid, lactic acid, malic acid, tartaric acid, fumaric acid, succinic acid, adipic acid, phytic acid, and gluconic acid. Specific examples of the free fatty acid include caprylic acid, lauric acid, myristic acid, palmitic acid, stearic acid, behenic acid, arachidic acid, palmitoleic acid, oleic acid, linoleic acid, α- and γ-linolenic acid, erucic acid, arachidonic acid, eicosapentaenoic acid, docosahexaenoic acid, and tetracosa tetraenoic acid obtained from animal and plant oils and fats such as tung oil, linseed oil, almond oil, inca inchi oil, perilla oil, olive oil, orange seed oil, pumpkin seed oil, kapok oil, mustard oil, *Trichosanthes kirilowii* seed oil, *Catalpa ovata* seed oil, a conjugated linoleic acid-containing oil or fat, *Calendula officinalis* seed oil, wheat germ oil, rice bran oil, corn oil, sesame oil, cherry seed oil, safflower oil, pomegranate seed oil, *Perilla frutescens* oil, snakeguard seed oil, soybean oil, tea seed oil, evening primrose seed oil, camellia oil, rapeseed oil, *Momordica charantia* seed oil, *Campsis grandiflora* seed oil, balsam apple seed oil, palm oil, sunflower oil, peanut oil, grape seed oil, *Impatiens balsamina* seed oil, macadamia nut oil, cottonseed oil, ground nut oil, beef tallow, lard, egg yolk oil, fish body oils obtained from sardine, salmon, mackerel, saury, herring, tuna, and other fishes, liver oils of squid and Alaska Pollack, orbital oils of bonito, tuna, and the like, seal oil, krill oil, an oil derived from *Schizochytrium* sp., an oil derived from *Nitzschia* sp., an oil derived from *Nannochloris* sp., and an oil derived from *Mortierella* sp. Among the above acids, the free fatty acids obtained from oils and fats derived from plants are preferred.

The method for measuring the acid value is not particularly limited, and an appropriately selected publicly known method for measuring the acid value may be used. For example, the acid value can be measured by the alkaline titration method, based on "Standard Methods for the Analysis of Fats, Oils and Related Materials, 4.2.1-1996, Acid Value" by The Japan Oil Chemists' Society.

The step 2 is a step of bringing the lecithin solution or lecithin dispersion obtained in the step 1 into contact with an adsorbent. The adsorbent may be, for example, an adsorbent used for refining oils and fats, and specific examples thereof include metal silicates, metal oxides such as alumina, an activated carbon, a zeolite, an activated clay, and a silica gel. These adsorbents may be used alone or in combination of two or more kinds thereof. Metal silicates are preferred. Specific examples of the metal silicate include magnesium silicate, calcium silicate, aluminum silicate, sodium silicate, potassium silicate, calcium aluminosilicate, calcium magnesium silicate, and sodium aluminosilicate. These metal silicates may be used alone or in combination of two or more kinds thereof. Among them, magnesium silicate, calcium silicate, calcium aluminosilicate, and sodium aluminosilicate are preferred, and magnesium silicate and calcium silicate are more preferred. The adsorbent may be a commercial product.

The method for bringing the lecithin solution or the lecithin dispersion into contact with the adsorbent is not particularly limited. Examples of the method include the method in which the adsorbent is added to the lecithin solution or the lecithin dispersion and mixed, and the mixture is stirred; and the method in which the lecithin solution or the lecithin dispersion is passed through a column and the like filled with the adsorbent. The contact duration is not particularly limited, and may be preferably about 0.1 second to 100 hours, more preferably about 1 minute to 24 hours, and still more preferably about 10 minutes to 30 minutes. The temperature of the lecithin solution or the lecithin dispersion during the contact with the adsorbent is not particularly limited, and may be preferably about −20 to 120° C., more preferably about 0 to 80° C., and still more preferably about 40 to 60° C.

The step 3 is a step of removing the adsorbent from the lecithin solution or the lecithin dispersion. The method for removing the adsorbent is not particularly limited, and a publicly known method for solid-liquid separation may be appropriately used. Specific examples thereof include filtration, centrifugal separation, centrifugal filtration, cyclone separation, filter press, screw press, and decantation.

The oligosaccharide content in the lecithin of the present invention is characteristically 50% by mass or more of that before the contact with the adsorbent. Moreover, the phosphatidylethanolamine content in the lecithin of the present invention is preferably 80% by mass or more of that before the contact with the adsorbent. It is known that the heat discoloration of lecithin is caused by an amino-carbonyl reaction, and methods for suppressing the heat discoloration by removing oligosaccharides and phosphatidylethanolamines from lecithin have been devised (for example, Patent Literature 2). However, oligosaccharides are derived from plants, animals, fish and shellfish, and the like, and are broadly present in nature. That is, when such a raw food material or a processed product thereof is cooked, not a little oligosaccharides exist therein. Therefore, even if oligosaccharides have been removed from lecithin as described in, for example, Patent Literature 2, oligosaccharides in the food material and phosphatidylethanolamines in the lecithin will contact in the cooking process, leading to heat discoloration. The lecithin of the present invention has, as its special feature, resistance to heat discoloration although the oligosaccharide content and the phosphatidylethanolamine content are not significantly decreased. Accordingly, the lecithin is useful in that oligosaccharides derived from food materials do not lead to heat discoloration.

The oligosaccharide content in the lecithin of the present invention may be about 50% by mass or more of that before the contact with the adsorbent, and may also be about 60% by mass or more, about 70% by mass or more, about 80% by mass or more, about 90% by mass or more, and almost equal (with almost no reduction). The method for measuring the oligosaccharide content in the lecithin is not particularly limited, and an appropriately selected publicly known method for measuring oligosaccharides may be used. Examples thereof include the HPLC method described later in Example 1 (5), in which a differential refractometer is used as a detector. Other detectors such as a fluorescence detector and an evaporative light scattering detector may also be used. Since various functions of lecithin are based on phospholipids contained in the lecithin, to compare each component in a lecithin with that in another lecithin, is important that the total phospholipid contents of the two lecithins match each other. Likewise, the oligosaccharide contents in lecithins needs to be compared after the total phospholipid contents before and after the contact with the adsorbent are adjusted to be the same. Examples of the method for measuring the phospholipid content in lecithin include "Standard Methods for the Analysis of Fats, Oils and Related Materials, 4.3.1-1996, Acetone Insoluble Matter", "Standard Methods for the Analysis of Fats, Oils and Related Materials, 4.3.3.1-1996, Phospholipid Composition (Thin-Layer Chromatography)", and "Standard Methods for the Analysis of Fats, Oils and Related Materials, 4.3.3.2-1996, Phospholipid Composition (High-Performance Liquid Chromatography)". The acetone insoluble matter and the total phospholipid content in the phospholipid composition can be taken as the phospholipid content in the lecithin.

The phosphatidylethanolamine content in the lecithin of the present invention is not particularly limited, and may be preferably about 80% by mass or more of that before the contact with the adsorbent, more preferably 90% by mass or more, and still more preferably 95% by mass or more. The phosphatidylethanolamine content in the lecithin of the present invention may be larger than that before the contact with the adsorbent. Examples of the method for measuring the phosphatidylethanolamine content in lecithin include "Standard Methods for the Analysis of Fats, Oils and Related Materials, 4.3.3.1-1996, Phospholipid Composition (Thin-Layer Chromatography)". In particular, a sample of lecithin is separated into its components by two-dimensional TLC, and the obtained spot of phosphatidylethanolamine is scraped off the silica gel thin-layer plate. Then, the amount of phosphorus is measured in accordance with "Standard Methods for the Analysis of Fats, Oils and Related Materials, 4.3.4-1996, Phosphorus (Wet Ashing)", and the phosphatidylethanolamine content in the total phospholipid can be obtained by the following formula.

Phosphatidylethanolamine content (%)=Amount of phosphorus in phosphatidylethanolamine fraction (mg/g)/Total amount of phosphorus (mg/g)

Other examples of the measurement method include "Standard Methods for the Analysis of Fats, Oils and Related Materials, 4.3.3.2-1996, Phospholipid Composition (High-Performance Liquid Chromatography)".

The lecithin solution or the lecithin dispersion from which the adsorbent has been removed in the step 3 may be used as it is or after additional purification, for various applications. For example, the lecithin from which the solvent or the dispersion medium has been removed may be obtained by concentrating and drying the lecithin solution or the lecithin dispersion from which the adsorbent has been removed. Furthermore, the lecithin solution or the lecithin dispersion may be purified to obtain a fractionated lecithin, which is obtained by subjecting lecithin of the present invention to solvent fractionation; an enzyme-degraded lecithin or an enzyme-treated lecithin, which is obtained by subjecting the lecithin to enzyme treatment; a hydrogenated lecithin, which is obtained by subjecting the lecithin to hydrogenation; an acetylated lecithin, which is obtained by subjecting the lecithin to acetylation; a hydroxylated lecithin, which is obtained by subjecting the lecithin to hydroxylation; or a lecithin obtained by a combination of solvent fractionation, enzyme treatment, hydrogenation, acetylation, and/or hydroxylation. The form of the lecithin of the present invention is not particularly limited, and may be any form such as a powder, a paste, and a lump. The lecithin of the present invention produced in this manner can be stably stored under the same conditions as those for an ordinary lecithin and an ordinary lecithin preparation.

The lecithin of the present invention has resistance to heat discoloration although oligosaccharides and phosphatidylethanolamine, which are considered to be causative substances of heat discoloration, are not significantly decreased. Accordingly the lecithin has an unexpected effect. Moreover, since the lecithin of the present invention has a phospholipid composition not significantly changed from that before the contact with the adsorbent (the phospholipid composition of the raw-material lecithin), the lecithin is extremely useful in that heat discoloration can be suppressed without impairing the original functions of lecithin based on phospholipids. Unlike conventional lecithins having resistance to heat discoloration, the lecithin of the present invention is not a modified lecithin, and complex processes for modifying lecithin are not required. Therefore, the lecithin of the present invention, which can be produced in a simple manner with fewer steps, is extremely useful.

The present invention provides an edible oil or fat containing the lecithin of the present invention. The edible oil or fat is not particularly limited, and a publicly known edible oil or fat derived from plants, animals, aquatic animals, microorganisms, and the like may be appropriately used. Specific examples of the oil or fat derived from a plant include tung oil, linseed oil, almond oil, inca inchi oil, perilla oil, olive oil, orange seed oil, pumpkin seed oil, kapok oil, mustard oil, *Trichosanthes kirilowii* seed oil, *Catalpa ovata* seed oil, a conjugated linoleic acid-containing oil or fat, *Calendula officinalis* seed oil, wheat germ oil, rice bran oil, corn oil, sesame oil, cherry seed oil, safflower oil, pomegranate seed oil, *Perilla frutescens* oil, snakeguard seed oil, soybean oil, tea seed oil, evening primrose seed oil, camellia oil, rapeseed oil, *Momordica charantia* seed oil, *Campsis grandiflora* seed oil, balsam apple seed oil, palm oil, sunflower oil, peanut oil, grape seed oil, *Impatiens balsamina* seed oil, macadamia nut oil, cottonseed oil, and ground nut oil. Specific examples of the oil or fat derived from an animal include beef tallow, lard, and egg yolk oil. Specific examples of the oil or fat derived from an aquatic animal include fish body oils obtained from sardine, salmon, mackerel, saury, herring, tuna, and other fishes, liver oils of squid and Alaska Pollack, orbital oils of bonito, tuna, and the like, seal oil, and krill oil. Specific examples of the oil or fat derived from a microorganism include an oil derived from *Schizochytrium* sp., an oil derived from *Nitzschia* sp., an oil derived from *Nannochloris* sp., and an oil derived from *Mortierella* sp. As a matter of course, a mixed oil or fat comprising two or more kinds of the above oils and fats, a hydrofined oil, a fractionated oil, a transesterified oil, and the like may also be used.

The lecithin content in the edible oil or fat is not particularly limited, and may be, for example, preferably 0.01 to 30% by mass, more preferably 0.5 to 15% by mass, and still more preferably 0.5 to 5.0% by mass.

The edible oil or fat of the present invention may be appropriately used for a stir-frying oil, a mold release oil, a fried rice oil, a frying oil, an oil or fat for noodles, an oil or fat for bread making, an oil or fat for confectionery, a flavor oil, and the like. The use of the edible oil or fat of the present invention for cooking can provide a high-quality food having suppressed heat discoloration.

The present invention provides food additives containing the lecithin of the present invention. Lecithin is used for food additives as a dispersing agent or an emulsifier for an oil-soluble component or a water-soluble component. In the process of producing food additives, the amount of a conventional lecithin is limited because heating and sterilization performed in the process cause heat discoloration of the lecithin. However, the use of the lecithin of the present invention can solve the problem of heat discoloration, and a food additive good in flavor and a preparation thereof can be prepared. Examples of the food additive include a manufacturing agent, an enzyme, a pH adjuster, a preservative, a sterilizer, an antioxidant, an antifungal agent, a shelf life improver, a colorant, a color improver, a decolorant, a brightener, a flavor, a spice extract, a sweetener, an acidulant, a seasoning, a bittering agent, an emulsifier, a thickener, a stabilizer, a gelatinizer, an adhesive paste, a leavening agent, a gum base, a yeast food, a softener, an enrichment, and preparations thereof.

The present invention provides cosmetics containing the lecithin of the present invention. Lecithin is used for cosmetics as a dispersing agent or an emulsifier for an oil-soluble component. In the process of producing cosmetics, the amount of a conventional lecithin is limited because heating and sterilization performed in the process cause heat discoloration of the lecithin. However, the use of the lecithin of the present invention can solve the problem of heat discoloration, and a cosmetic of which color is lighter compared to that of a cosmetic containing a conventional lecithin can be produced. Cosmetics include a so-called medicated cosmetic (quasi drug). Examples of the cosmetic include a cleanser, a shampoo, a conditioner, a hair tonic, a hair lotion, an after-shave lotion, a body lotion, a cosmetic lotion, a cleansing cream, a massage cream, an emollient cream, an aerosol product, an air refresher, an aromatic, a deodorant, and a bath additive. The cosmetic of the present invention may contain, in addition to the lecithin of the present invention, components typically used for cosmetics, such as a surface-active agent, a humectant, an oil or fat derived from an animal and a plant, an oil or fat derived from a microorganism, silicones, a higher alcohol, a lower alcohol, an extract derived from an animal and a plant, an extract derived from a microorganism, an ultraviolet absorber, an antiphlogistic, a sequestering agent, vitamins, an antioxidant, a thickener, a preservative, a disinfectant, a pH adjuster, a colorant, and a range or flavors as appropriate in accordance with a purpose.

The present invention provides a medicine containing the lecithin of the present invention. Although lecithin is used as an emulsifier for medicines, its use has been limited in some cases where heating is performed in the production process. However, the use of the lecithin of the present invention can solve the problem of heat discoloration. The medicine contains active ingredients in addition to the lecithin of the present invention and may further contain pharmaceutically acceptable carriers and additives as appropriate to give a formulation. In particular, the medicine may be formulated into oral preparations such as a tablet, a coated tablet, a pill, a powder, a granule, a capsule, a liquid, a suspension, and an emulsion; and parenteral preparations such as an injection, an infusion solution, a suppository, an ointment, and a patch. The blending ratio of a carrier or an additive may be set appropriately based on the range typically adopted in the pharmaceutical field. The carrier or the additive which can be contained is not particularly limited, and examples thereof include various carriers such as water, physiological saline, other aqueous solvents, and an aqueous or oily base; and various additives such as an excipient, a binder, a pH adjuster, a disintegrant, an absorption promoter, a lubricant, a colorant, a flavoring agent, and a flavor.

The present invention provides a feed containing the lecithin of the present invention. Although lecithin is used as an emulsifier for feeds or used for imparting a physiological function such as the improvement of lipid metabolism to feeds, its use has been limited in some cases where heating is performed in the production process. However, the use of the lecithin of the present invention can solve the problem of heat discoloration. Examples of the feed include a feed for livestock such as a cow, a horse, and a pig; a feed for poultry such as a chicken; a feed for cultured fish and shellfish; and a feed for pet animals such as a dog and a cat. The feed of the present invention may be processed and manufactured by a general method for producing feeds, except for the addition of the lecithin of the present invention to the feeds.

The present invention provides an industrial product containing the lecithin of the present invention. Although lecithin is used as a surface-active agent, an antioxidant, a release agent, and the like, for industrial products, its use has been limited in some cases where heating is performed. However, the use of the lecithin of the present invention can solve the problem of heat discoloration. Examples of the industrial product include coating materials (such as a paint, a varnish, a lacquer, an enamel, an ink, a photosensitizing agent, and a car wax), petroleum products (such as a lubricant, a grease, a cutting oil, a fuel oil, and a brake oil), agricultural chemicals (such as an antifungal agent and a control agent), resin products (such as a rubber and a plastic), magnetic products (such as a magnetic card and a magnetic tape), a leather product, and a fabric.

The present invention provides a food or drink containing the above edible oil or fat and/or the above food additive of the present invention. The food or drink includes a health food, a functional food, a food for specified health use, and a food for the sick. The form of the food or drink is not particularly limited. Specific examples thereof include so-called nutraceutical foods or dietary supplements such as a tablet, a granule, a powder, and a health drink. Other examples include drinks such as tea drink, refreshing drink, soda, nutritional drink, fruit juice, and lactic drink; noodles such as buckwheat noodle, wheat noodle, Chinese noodle, and instant noodle; sweets and bakery products such as candy, gum, chocolate, snack, biscuit, jelly, jam, cream, baked goods, and bread; fishery or livestock products such as fish sausage, ham, and sausage; dairy products such as processed milk and fermented milk; fats, oils, and processed foods thereof, such as salad oil, oil for frying, margarine, mayonnaise, shortening, whipped cream, and dressing; seasonings such as sauce and dipping sauce; retort pouch foods such as curry, stew, sauce for rice-bowl cuisine, porridge, and rice soup; and frozen desserts such as ice cream, sherbet, and shaved ice.

The present invention includes a method for suppressing heat discoloration of lecithin, characterized in that the lecithin of the present invention is used. The present invention also includes a method for suppressing heat discoloration of an edible oil or fat containing lecithin, characterized in that the lecithin of the present invention is contained in the edible oil or fat.

EXAMPLES

The present invention will be described in detail with reference to Examples hereinbelow, but the present invention is not limited to them.

Example 1

Suppression of Heat Discoloration of Soybean Lecithin Paste (1) Experimental Material Soybean lecithin paste: SLP-PASTE (trade name, manufactured by Tsuji Oil Mills Co., Ltd.)

Soybean sirasimeyu (Soybean refined oil) (manufactured by Tsuji Oil Mills Co., Ltd.)

Fatty acid: TFA-130 (trade name, manufactured by Tsuno Food Industrial Co., Ltd.)

Magnesium silicate: Dalsorb F50 (manufactured by the Dallas Group of America, Inc.)

(2) Adjustment of Acid Value and Total Phospholipid Content in SLP-PASTE

SLP-PASTE, soybean sirasimeyu (soybean refined oil), and TFA-130 in the amounts shown in Table 1 were weighed out and were placed in a 70-ml bottle. The mixture was stirred with heating at a temperature of 60° C. for 30 minutes. The acid value (mgKOH/g) and the total phospholipid content (% by mass) in each sample (Pastes 1 to 6) were measured in accordance with "Acid Value (4.2.1-1996)" and "Phospholipid Composition (Thin-Layer Chromatography, 4.3.3.1-1996)" described in "Standard Methods for the Analysis of Fats, Oils and Related Materials".

In particular, in order to determine the acid value, the sample was dissolved in petroleum ether to prepare Solution 1. Phenolphthalein as an indicator was added to ethanol to prepare a solution, and 0.1 mol/L potassium hydroxide ethanol standard solution was dropped in the solution for neutralization to prepare Solution 2. Then Solution 2 was added to Solution 1, and the mixed solution was titrated with 0.1 mol/L potassium hydroxide ethanol standard solution. The acid value was calculated based on the amount of the 0.1 mol/L potassium hydroxide ethanol standard solution used in the titration. Separately, in order to determine the total phospholipid content, the sample was dissolved in chloroform to prepare a solution. Then the solution was applied onto the lower right end of a 100 mm×100 mm silica gel thin-layer plate, and was developed with Developing Solvent A (chloroform/methanol/ammonia=130:60:8). After drying of the solvent on the silica gel thin-layer plate, the thin-layer plate was rotated by 90 degrees clockwise, and the sample was developed with Developing Solvent B (chloroform/methanol/acetic acid/purified water=170:25:25:6). After drying of the solvent on the silica gel thin-layer plate, the spots of each phospholipid were visualized by the color development with sulfuric acid. After a phospholipid fraction of interest was scraped off the silica gel thin-layer plate, the amount of phosphorus was measured in accordance with "Standard Methods for the Analysis of Fats, Oils and Related Materials, 4.3.4-1996, Phosphorus (Wet Ashing)", and each phospholipid content was calculated by the following formula.

Phospholipid content (%)=Amount of phosphorus in phospholipid fraction (mg/g)/Total amount of phosphorus (mg/g)

The measurement results of the acid value and the total phospholipid content in each sample (Pastes 1 to 6) are shown in Table 2.

TABLE 1

| Sample | Paste 1 | Paste 2 | Paste 3 | Paste 4 | Paste 5 | Paste 6 |
| --- | --- | --- | --- | --- | --- | --- |
| SLP-PASTE | 12.05 g | 12.05 g | 12.05 g | 12.05 g | 12.05 g | 12.05 g |
| Soybean sirasimeyu (Soybean refined oil) | 17.95 g | 17.24 g | 16.44 g | 15.63 g | 14.82 g | 14.02 g |
| TFA-130 | — | 0.71 g | 1.51 g | 2.32 g | 3.13 g | 3.93 g |
| Total | 30.00 g | 30.00 g | 30.00 g | 30.00 g | 30.00 g | 30.00 g |

TABLE 2

| Sample | Paste 1 | Paste 2 | Paste 3 | Paste 4 | Paste 5 | Paste 6 |
| --- | --- | --- | --- | --- | --- | --- |
| Acid value | 7.5 mgKOH/g | 14.4 mgKOH/g | 19.6 mgKOH/g | 25.0 mgKOH/g | 29.9 mgKOH/g | 35.0 mgKOH/g |
| Total phospholipid content | 25.0% | 25.0% | 25.0% | 25.0% | 25.0% | 25.0% |

(3) Magnesium Silicate Treatment to SLP-PASTE with Varied Acid Value and Total Phospholipid Each sample (Pastes 1 to 6, 20.00 g each) and Dalsorb F50 (3.00 g) were placed in a 70-ml bottle and stirred with heating at a temperature of 60° C. for 30 minutes. Dalsorb F50 was removed by pressure filtration, and the obtained filtrate was vacuum-dried (50° C., −0.09 MPa, 18 hours). Pastes 1 to 6 after the magnesium silicate treatment are named Pastes 7 to 12, respectively. The acid value and the total phospholipid content in Pastes 7 to 12, obtained after the magnesium silicate treatment, were measured in accordance with "Acid Value (4.2.1-1996)" and "Phospholipid Composition (Thin-Layer Chromatography, 4.3.3.1-1996)" described in "Standard Methods for the Analysis of Fats, Oils and Related Materials".

The measurement results of the acid value and the total phospholipid content in each sample (Pastes 7 to 12) are shown in Table 3.

TABLE 3

| Sample | Paste 7 | Paste 8 | Paste 9 | Paste 10 | Paste 11 | Paste 12 |
| --- | --- | --- | --- | --- | --- | --- |
| Recovery amount | 14.33 g | 14.29 g | 13.70 g | 14.39 g | 14.45 g | 14.08 g |
| Yield | 71.6% | 71.5% | 68.5% | 72.0% | 72.3% | 70.4% |
| Acid value | 10.3 mgKOH/g | 10.3 mgKOH/g | 16.7 mgKOH/g | 21.74 mgKOH/g | 27.42 mgKOH/g | 33.0 mgKOH/g |
| Total phospholipid content | 22.6% | 17.5% | 16.9% | 18.1% | 18.3% | 17.4% |

(4) Change in Phospholipid Composition Before and After Magnesium Silicate Treatment The phospholipid compositions of Pastes 3 and 9 were compared with each other, and also those of Pastes 6 and 12 were compared with each other. The phospholipid composition in each sample was measured in accordance with "Phospholipid Composition (Thin-Layer Chromatography, 4.3.3.1-1996)" described in "Standard Methods for the Analysis of Fats, Oils and Related Materials". In particular, the sample was dissolved in chloroform to prepare a solution, and the solution was applied onto the lower right end of a 100 mm×100 mm silica gel thin-layer plate, and was developed with Developing Solvent A (chloroform/methanol/ammonia=130:60:8). After drying of the solvent on the silica gel thin-layer plate, the thin-layer plate was rotated by 90 degrees clockwise, and the sample was developed with Developing Solvent B (chloroform/methanol/acetic acid/purified water=170:25:25:6). After drying of the solvent on the silica gel thin-layer plate, the spots of each phospholipid were visualized by the color development with sulfuric acid. After a phospholipid fraction of interest was scraped off the silica gel thin-layer plate, the amount of phosphorus was measured in accordance with "Standard Methods for the Analysis of Fats, Oils and Related Materials, 4.3.4-1996, Phosphorus (Wet Ashing)", and the phospholipid composition was calculated from the amount of phosphorus.

The results are shown in Table 4. In Table 4, PC represents phosphatidylcholine, PE represents phosphatidylethanolamine, PA represents phosphatidic acid, PI represents phosphatidylinositol, and LPC represents lysophosphatidylcholine. As shown in Table 4, it was confirmed that PE, considered to be a causative substance of heat discoloration, had not been reduced by the magnesium silicate treatment.

TABLE 4

| Sample | | Paste 3 | Paste 9 | Paste 6 | Paste 12 |
|---|---|---|---|---|---|
| Magnesium silicate treatment | | Untreated | Treated | Untreated | Treated |
| Acid value | | 19.6 | 16.7 | 35 | 33 |
| Phospholipid composition | Total phospholipid content | 25.0% | 16.9% | 25.0% | 17.4% |
| | PC | 33.5% | 27.4% | 34.1% | 27.9% |
| | PE | 28.4% | 31.0% | 27.8% | 33.0% |
| | PA | 5.2% | 5.9% | 5.6% | 6.4% |
| | PI | 15.4% | 17.5% | 16.4% | 18.2% |
| | LPC | 1.1% | 0.3% | 1.0% | 1.1% |
| | Decomposition product of phospholipid | 3.0% | 2.5% | 2.9% | 1.8% |

(5) Change in Oligosaccharide Content Before and After Magnesium Silicate Treatment The oligosaccharide contents before and after the magnesium silicate treatment were compared using all the samples (Pastes 1 to 12). The oligosaccharide content (% by mass) in the lecithin was measured by the following method.

Each sample (Pastes 1 to 12, total amount of phospholipids: 0.25 g) was subjected to liquid-liquid partition with Hexane (12.5 ml) and a 60% ethanol-water solution (12.5 ml) to obtain a 60% ethanol-water fraction. Then, the remaining hexane fraction was subjected again to liquid-liquid partition with a 60% ethanol-water solution (12.5 ml) to obtain a 60% ethanol-water fraction. This procedure was performed 4 times in total, and the 60% ethanol-water fraction containing water soluble matter was concentrated and vacuum-dried. The obtained dry matter of the 60% ethanol-water fraction was redissolved in water, the solution was applied to Sep-Pak (ODS), and then elution with 10 ml of water was performed. The obtained water fraction was concentrated and vacuum-dried. Furthermore, the obtained dry matter of the water fraction was redissolved in water, the solution was applied to Sep-Pak ($NH_2$), and then elution with 10 ml of a 75% acetonitrile-water solution was performed. The obtained 75% acetonitrile-water solution was concentrated and vacuum-dried, and then quantitatively analyzed by HPLC. The conditions for HPLC analysis are shown below.

<HPLC Analysis Conditions>

Pump: SHIMADZU LC-10AD

Detector: SHIMADZU RID-10A

Column: Nacalai tesque COSMOSIL 5NH2-MS 250 mm×10 mm i.d.

Flow rate: 4.0 ml/min

Mobile phase: 75% $CH_3CN$/water

The results are shown in Table 5. Oligosaccharides, considered to be causative substances of heat discoloration, remained at a high rate even after the magnesium silicate treatment.

TABLE 5

| Sample | Magnesium silicate treatment | Oligosaccharide content | Oligosaccharide residual rate |
|---|---|---|---|
| Paste 1 | Untreated | 3.6% | 69.4% |
| Paste 7 | Treated | 2.5% | |
| Paste 2 | Untreated | 4.1% | 85.4% |
| Paste 8 | Treated | 3.5% | |
| Paste 3 | Untreated | 4.3% | 72.1% |
| Paste 9 | Treated | 3.1% | |
| Paste 4 | Untreated | 4.2% | 85.7% |
| Paste 10 | Treated | 3.6% | |
| Paste 5 | Untreated | 4.6% | 82.6% |
| Paste 11 | Treated | 3.8% | |
| Paste 6 | Untreated | 4.5% | 95.2% |
| Paste 12 | Treated | 4.3% | |

(6) Heat-Discoloration Test

Each of Pastes 1 to 12 (1 to 6: samples before the magnesium silicate treatment, 7 to 12: samples after the magnesium silicate treatment) and soybean sirasimeyu (soybean refined oil) in the amounts shown in Table 6 were weighed out in order that the total phospholipid content may be 1% by mass, and were placed in a 30-ml bottle. The mixture was stirred with heating at a temperature of 60° C. for 10 minutes. Then 6 g of each prepared sample was placed separately in a test tube, and was heated at a temperature of 200° C. for 15 minutes.

TABLE 6

| Sample | Paste 1 | Paste 2 | Paste 3 | Paste 4 | Paste 5 | Paste 6 |
|---|---|---|---|---|---|---|
| Lecithin | 0.40 g | 0.40 g | 0.40 g | 0.40 g | 0.40 g | 0.40 g |
| Soybean sirasimeyu (Soybean refined oil) | 9.60 g | 9.60 g | 9.60 g | 9.60 g | 9.60 g | 9.60 g |
| Total | 10.00 g | 10.00 g | 10.00 g | 10.00 g | 10.00 g | 10.00 g |

TABLE 6-continued

| Sample | Paste 7 | Paste 8 | Paste 9 | Paste 10 | Paste 11 | Paste 12 |
|---|---|---|---|---|---|---|
| Lecithin | 0.44 g | 0.57 g | 0.59 g | 0.55 g | 0.55 g | 0.56 g |
| Soybean sirasimeyu (Soybean refined oil) | 9.56 g | 9.43 g | 9.41 g | 9.45 g | 9.45 g | 9.44 g |
| Total | 10.00 g | 10.00 g | 10.00 g | 10.00 g | 10.00 g | 10.00 g |

Each of the samples (Pastes 1 to 12) after heating was measured for hues in accordance with "Standard Methods for the Analysis of Fats, Oils and Related Materials, 2.2.1.1-1996, Color (Lovibond Method)". The obtained values of hues were assigned to the formula:

"10×B+1×Y+10×R"

to give a numerical value.

The results are shown in FIG. 1. A higher acid value of a sample before the magnesium silicate treatment resulted in a higher rate of suppression of discoloration.

Example 2

Suppression of Heat Discoloration in Fractionated Lecithin Paste (1) Experimental Material Fractionated lecithin paste: SLP-PC35 (trade name, manufactured by Tsuji Oil Mills Co., Ltd., a lecithin containing 35% of PC (phosphatidylcholine) and having excellent fluidity)

Soybean sirasimeyu (Soybean refined oil) (manufactured by Tsuji Oil Mills Co., Ltd.)

Fatty acid: TFA-130 (trade name, manufactured by Tsuno Food Industrial Co., Ltd.)

Magnesium silicate: Dalsorb F50 (manufactured by the Dallas Group of America, Inc.)

(2) Adjustment of Acid Value and Total Phospholipid Content in SLP-PC35

SLP-PC35, soybean sirasimeyu (soybean refined oil), and TFA-130 in the amounts shown in Table 7 were weighed out and were placed in a 70-ml bottle. The mixture was stirred with heating at a temperature of 60° C. for 30 minutes. The acid value (mgKOH/g) and the total phospholipid content (% by mass) in each sample (PC35-1 to 6) were measured in a similar manner to that in Example 1, in accordance with "Acid Value (4.2.1-1996)" and "Phospholipid Composition (Thin-Layer Chromatography, 4.3.3.1-1996)" described in "Standard Methods for the Analysis of Fats, Oils and Related Materials". The measurement results of the acid value and the total phospholipid content in each sample (PC35-1 to 6) are shown in Table 8.

TABLE 7

| Sample | PC35-1 | PC35-2 | PC35-3 | PC35-4 | PC35-5 | PC35-6 |
|---|---|---|---|---|---|---|
| SLP-PC35 | 22.98 g | 22.98 g | 22.98 g | 22.98 g | 22.98 g | 22.98 g |
| Soybean sirasimeyu (Soybean refined oil) | 27.02 g | 25.33 g | 24.00 g | 22.67 g | 21.34 g | 20.01 g |
| TFA-130 | — | 1.69 g | 3.02 g | 4.35 g | 5.68 g | 7.01 g |
| Total | 50.00 g | 50.00 g | 50.00 g | 50.00 g | 50.00 g | 50.00 g |

TABLE 8

| Sample | PC35-1 | PC35-2 | PC35-3 | PC35-4 | PC35-5 | PC35-6 |
|---|---|---|---|---|---|---|
| Acid value | 8.0 mgKOH/g | 14.2 mgKOH/g | 19.3 mgKOH/g | 24.8 mgKOH/g | 29.5 mgKOH/g | 34.9 mgKOH/g |
| Total phospholipid content | 25.0% | 25.0% | 25.0% | 25.0% | 25.0% | 25.0% |

(3) Magnesium Silicate Treatment to SLP-PC35 with Varied Acid Value and Total Phospholipid Each sample (PC35-1 to 6, 20.00 g each) and Dalsorb F50 (3.00 g) were placed in a 70-ml bottle and stirred with heating at a temperature of 60° C. for 30 minutes. Dalsorb F50 was removed by pressure filtration, and the obtained filtrate was vacuum-dried (50° C., −0.09 MPa, 18 hours). PC35-1 to 6 after the magnesium silicate treatment are named PC35-7 to 12, respectively. The acid value and the total phospholipid content in PC35-7 to 12, obtained after the magnesium silicate treatment, were measured in a similar manner to that in Example 1, in accordance with "Acid Value (4.2.1-1996)" and "Phospholipid Composition (Thin-Layer Chromatography, 4.3.3.1-1996)" described in "Standard Methods for the Analysis of Fats, Oils and Related Materials". The measurement results of the acid value and the total phospholipid content in each sample (PC35-7 to 12) are shown in Table 9.

TABLE 9

| Sample | PC35-7 | PC35-8 | PC35-9 | PC35-10 | PC35-11 | PC35-12 |
|---|---|---|---|---|---|---|
| Recovery amount | 13.25 g | 14.94 g | 15.01 g | 14.90 g | 15.22 g | 14.85 g |

TABLE 9-continued

| Sample | PC35-7 | PC35-8 | PC35-9 | PC35-10 | PC35-11 | PC35-12 |
|---|---|---|---|---|---|---|
| Yield | 66.3% | 74.7% | 75.1% | 74.5% | 76.1% | 74.3% |
| Acid value | 4.9 mgKOH/g | 12.4 mgKOH/g | 17.4 mgKOH/g | 22.3 mgKOH/g | 27.1 mgKOH/g | 32.3 mgKOH/g |
| Total phospholipid content | 15.4% | 22.5% | 23.0% | 22.7% | 23.1% | 23.1% |

(4) Heat-Discoloration Test

Each of PC35-1 to 12 (1 to 6: samples before the magnesium silicate treatment, 7 to 12: samples after the magnesium silicate treatment) and soybean sirasimeyu (soybean refined oil) in the amounts shown in Table 10 were weighed out in order that the total phospholipid content may be 1% by mass, and were placed in a 30-ml bottle. The mixture was stirred with heating at a temperature of 60° C. for 10 minutes. Then 6 g of each prepared sample was placed separately in a test tube, and was heated at a temperature of 200° C. for 15 minutes.

TABLE 10

| Sample | PC35-1 | PC35-2 | PC35-3 | PC35-4 | PC35-5 | PC35-6 |
|---|---|---|---|---|---|---|
| Lecithin | 0.40 g | 0.40 g | 0.40 g | 0.40 g | 0.40 g | 0.40 g |
| Soybean sirasimeyu (Soybean refined oil) | 9.60 g | 9.60 g | 9.60 g | 9.60 g | 9.60 g | 9.60 g |
| Total | 10.00 g | 10.00 g | 10.00 g | 10.00 g | 10.00 g | 10.00 g |

| Sample | PC35-7 | PC35-8 | PC35-9 | PC35-10 | PC35-11 | PC35-12 |
|---|---|---|---|---|---|---|
| Lecithin | 0.65 g | 0.44 g | 0.44 g | 0.44 g | 0.43 g | 0.43 g |
| Soybean sirasimeyu (Soybean refined oil) | 9.35 g | 9.56 g | 9.56 g | 9.56 g | 9.57 g | 9.57 g |
| Total | 10.00 g | 10.00 g | 10.00 g | 10.00 g | 10.00 g | 10.00 g |

Each of the samples (PC35-1 to 12) after heating was measured for hues in accordance with "Standard Methods for the Analysis of Fats, Oils and Related Materials, 2.2.1.1-1996, Color (Lovibond Method)". The obtained values of hues were assigned to the formula:

"10×B+1×Y+10×R"

to give a numerical value.

The results are shown in FIG. 2. A higher acid value of a sample before the magnesium silicate treatment resulted in a higher rate of suppression of discoloration.

Example 3

Suppression of Heat Discoloration in Fractionated Lecithin Lump (1) Experimental Material Fractionated lecithin lump: SLP-PC70 (trade name, manufactured by Tsuji Oil Mills Co., Ltd., a fractionated lecithin containing 70% of PC (phosphatidylcholine) and having good solubility in water as well as in oils and fats)

Soybean sirasimeyu (Soybean refined oil) (manufactured by Tsuji Oil Mills Co., Ltd.)

Fatty acid: TFA-130 (trade name, manufactured by Tsuno Food Industrial Co., Ltd.)

Magnesium silicate: Dalsorb F50 (manufactured by the Dallas Group of America, Inc.)

(2) Adjustment of Acid Value and Total Phospholipid Content in SLP-PC70

SLP-PC70, soybean sirasimeyu (soybean refined oil), and TFA-130 in the amounts shown in Table 11 were weighed out and were placed in a 70-ml bottle. The mixture was stirred with heating at a temperature of 60° C. for 30 minutes. The acid value (mgKOH/g) and the total phospholipid content (% by mass) in each sample (PC70-1 to 6) were measured in a similar manner to that in Example 1, in accordance with "Acid Value (4.2.1-1996)" and "Phospholipid Composition (Thin-Layer Chromatography, 4.3.3.1-1996)" described in "Standard Methods for the Analysis of Fats, Oils and Related Materials". The measurement results of the acid value and the total phospholipid content in each PC70 sample (PC70-1 to 6) are shown in Table 12.

TABLE 11

| Sample | PC70-1 | PC70-2 | PC70-3 | PC70-4 | PC70-5 | PC70-6 |
|---|---|---|---|---|---|---|
| SLP-PC70 | 12.92 g | 12.92 g | 12.92 g | 12.92 g | 12.92 g | 12.92 g |
| Soybean sirasimeyu (Soybean refined oil) | 35.18 g | 33.85 g | 32.52 g | 31.20 g | 29.87 g | 28.54 g |
| TFA-130 | 1.90 g | 3.23 g | 4.56 g | 5.88 g | 7.21 g | 8.54 g |
| Total | 50.00 g | 50.00 g | 50.00 g | 50.00 g | 50.00 g | 50.00 g |

TABLE 12

| Sample | PC70-1 | PC70-2 | PC70-3 | PC70-4 | PC70-5 | PC70-6 |
|---|---|---|---|---|---|---|
| Acid value | 9.4 mgKOH/g | 14.7 mgKOH/g | 19.6 mgKOH/g | 24.9 mgKOH/g | 29.6 mgKOH/g | 34.7 mgKOH/g |
| Total phospholipid content | 25.0% | 25.0% | 25.0% | 25.0% | 25.0% | 25.0% |

(3) Magnesium Silicate Treatment to SLP-PC70 with Varied Acid Value and Total Phospholipid Each sample (PC70-1 to 6, 20.00 g each) and Dalsorb F50 (3.00 g) were placed in a 70-ml bottle and stirred with heating at a temperature of 60° C. for 30 minutes. Dalsorb F50 was removed by pressure filtration, and the obtained filtrate was vacuum-dried (50° C., −0.09 MPa, 18 hours). PC70-1 to 6 after the magnesium silicate treatment are named PC70-7 to 12, respectively. The acid value and the total phospholipid content in PC70-7 to 12, obtained after the magnesium silicate treatment, were measured in a similar manner to that in Example 1, in accordance with "Acid Value (4.2.1-1996)" and "Phospholipid Composition (Thin-Layer Chromatography, 4.3.3.1-1996)" described in "Standard Methods for the Analysis of Fats, Oils and Related Materials". The measurement results of the acid value and the total phospholipid content in each PC70 sample (PC70-7 to 12) are shown in Table 13.

TABLE 13

| Sample | PC70-7 | PC70-8 | PC70-9 | PC70-10 | PC70-11 | PC70-12 |
|---|---|---|---|---|---|---|
| Recovery amount | 14.96 g | 14.88 g | 15.26 g | 15.05 g | 14.80 g | 14.97 g |
| Yield | 74.8% | 74.4% | 76.3% | 75.3% | 74.0% | 74.9% |
| Acid value | 7.8 mgKOH/g | 12.9 mgKOH/g | 17.8 mgKOH/g | 22.6 mgKOH/g | 27.9 mgKOH/g | 32.4 mgKOH/g |
| Total phospholipid content | 19.9% | 21.7% | 22.0% | 21.9% | 22.2% | 22.0% |

(4) Heat-Discoloration Test

Each of PC70-1 to 12 (1 to 6: samples before the magnesium silicate treatment, 7 to 12: samples after the magnesium silicate treatment) and soybean sirasimeyu (soybean refined oil) in the amounts shown in Table 14 were weighed out in order that the total phospholipid content may be 1% by mass, and were placed in a 30-ml bottle. The mixture was stirred with heating at a temperature of 60° C. for 10 minutes. Then 6 g of each prepared sample was placed separately in a test tube, and was heated at a temperature of 200° C. for 15 minutes.

TABLE 14

| Sample | PC70-1 | PC70-2 | PC70-3 | PC70-4 | PC70-5 | PC70-6 |
|---|---|---|---|---|---|---|
| Lecithin | 0.40 g | 0.40 g | 0.40 g | 0.40 g | 0.40 g | 0.40 g |
| Soybean sirasimeyu (Soybean refined oil) | 9.60 g | 9.60 g | 9.60 g | 9.60 g | 9.60 g | 9.60 g |
| Total | 10.00 g | 10.00 g | 10.00 g | 10.00 g | 10.00 g | 10.00 g |

| Sample | PC70-7 | PC70-8 | PC70-9 | PC70-10 | PC70-11 | PC70-12 |
|---|---|---|---|---|---|---|
| Lecithin | 0.50 g | 0.46 g | 0.45 g | 0.46 g | 0.45 g | 0.46 g |
| Soybean sirasimeyu (Soybean refined oil) | 9.50 g | 9.54 g | 9.55 g | 9.54 g | 9.55 g | 9.54 g |
| Total | 10.00 g | 10.00 g | 10.00 g | 10.00 g | 10.00 g | 10.00 g |

Each of the samples (PC70-1 to 12) after heating was measured for hues in accordance with "Standard Methods for the Analysis of Fats, Oils and Related Materials, 2.2.1.1-1996, Color (Lovibond Method)". The obtained values of hues were assigned to the formula:

"10×B+1×Y+10×R"

to give a numerical value.

The results are shown in FIG. 3. A higher acid value of a sample before the magnesium silicate treatment resulted in a higher rate of suppression of discoloration.

Example 4

Suppression of Heat Discoloration in Soybean Lecithin Paste (1) Experimental Material Soybean lecithin paste: SLP-PASTE (trade name, manufactured by Tsuji Oil Mills Co., Ltd.)

Soybean sirasimeyu (Soybean refined oil) (manufactured by Tsuji Oil Mills Co., Ltd.)

Fatty acid: TFA-130 (trade name, manufactured by Tsuno Food Industrial Co., Ltd.)

Calcium silicate: BRISKOIL CAS-30S (trade name, manufactured by Tomita Pharmaceutical CO., Ltd.)

(2) Adjustment of Acid Value and Total Phospholipid Content in SLP-PASTE

Samples (Pastes 13 and 14) were prepared in a similar manner to that for Pastes 1 and 6 in Example 1. The acid value (mgKOH/g) and the total phospholipid content (% by mass) in each sample were measured in a similar manner to that in Example 1, in accordance with "Acid Value (4.2.1-1996)" and "Phospholipid Composition (Thin-Layer Chromatography, 4.3.3.1-1996)" described in "Standard Methods for the Analysis of Fats, Oils and Related Materials".

The measurement results of the acid value and the total phospholipid content in each sample (Pastes 13 and 14) are shown in Table 15.

TABLE 15

| Sample | Paste 13 | Paste 14 |
| --- | --- | --- |
| Acid value | 9.9 mgKOH/g | 35.1 mgKOH/g |
| Total phospholipid content | 25.0% | 25.0% |

(3) Calcium Silicate Treatment to SLP-PASTE with Varied Acid Value and Total Phospholipid Adsorbent treatment was performed in a similar manner to that in Example 1, except that calcium silicate was used in place of magnesium silicate. Pastes 13 and 14 after the calcium silicate treatment are named Pastes 15 and 16, respectively. The acid value and the total phospholipid content in Pastes 15 and 16, obtained after the calcium silicate treatment, were measured in a similar manner to that in Example 1, in accordance with "Acid Value (4.2.1-1996)" and "Phospholipid Composition (Thin-Layer Chromatography, 4.3.3.1-1996)" described in "Standard Methods for the Analysis of Fats, Oils and Related Materials".

The measurement results of the acid value and the total phospholipid content in each sample (Pastes 15 and 16) are shown in Table 16.

TABLE 16

| Sample | Paste 15 | Paste 16 |
| --- | --- | --- |
| Recovery amount | 13.59 g | 13.60 g |
| Yield | 68.0% | 68.0% |
| Acid value | 5.1 mgKOH/g | 11.1 mgKOH/g |
| Total phospholipid content | 20.8% | 21.8% |

(4) Heat-Discoloration Test

Each of Pastes 13 to 16 (13 and 14: samples before the calcium silicate treatment, 15 and 16: samples after the calcium silicate treatment) and soybean sirasimeyu (soybean refined oil) in the amounts shown in Table 17 were weighed out in order that the total phospholipid content may be 1% by mass, and were placed in a 30-ml bottle. The mixture was stirred with heating at a temperature of 60° C. for 10 minutes. Then 6 g of each prepared sample was placed separately in a test tube, and was heated at a temperature of 200° C. for 15 minutes.

TABLE 17

| Sample | Paste 13 | Paste 14 |
| --- | --- | --- |
| Lecithin | 0.40 g | 0.40 g |
| Soybean sirasimeyu (Soybean refined oil) | 9.60 g | 9.60 g |
| Total | 10.00 g | 10.00 g |

| Sample | Paste 15 | Paste 16 |
| --- | --- | --- |
| Lecithin | 0.48 g | 0.46 g |
| Soybean sirasimeyu (Soybean refined oil) | 9.52 g | 9.54 g |
| Total | 10.00 g | 10.00 g |

Each of the samples (Pastes 13 to 16) after heating was measured for hues in accordance with "Standard Methods for the Analysis of Fats, Oils and Related Materials, 2.2.1.1-1996, Color (Lovibond Method)". The obtained values of hues were assigned to the formula:

"10×B+1×Y+10×R"

to give a numerical value.

Figure 4:
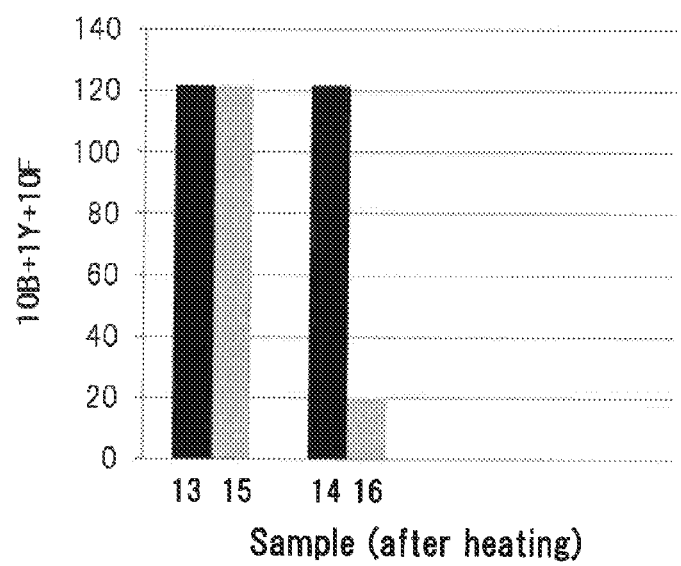
FIG. 4 shows the examination results of the suppressing effect of calcium silicate treatment on discoloration of soybean lecithin paste (trade name: SLP-PASTE, manufactured by Tsuji Oil Mills Co., Ltd.).

The results are shown in FIG. 4. A higher acid value of a sample before the calcium silicate treatment resulted in a higher rate of suppression of discoloration.

The present invention is not limited to each of the embodiments and examples described above and can be variously modified within the scope of claims. The technical scope of the present invention encompasses embodiments obtained by appropriately combining different technical means disclosed in respective embodiments.

The invention claimed is:

1. A method for producing a lecithin or lecithin preparation having resistance to heat discoloration comprising:
   step 1: dispersing a lecithin in a dispersion medium to prepare a lecithin dispersion and adjusting the acid value of the lecithin dispersion,
     wherein the lecithin dispersion is prepared by using an oil or fat as the dispersion medium;

step 2: bringing the obtained lecithin dispersion by the step 1 into contact with an adsorbent; and step 3: removing the adsorbent from the lecithin dispersion after the step 2, wherein the adjusting the acid value is performed by addition of an acid to the lecithin dispersion, and wherein the acid is one or more free fatty acid selected from the group consisting of caprylic acid, lauric acid, myristic acid, palmitic acid, stearic acid, behenic acid, arachidic acid, palmitoleic acid, oleic acid, linoleic acid, α- and γ-linolenic acid, erucic acid, arachidonic acid, eicosapentaenoic acid, docosahexaenoic acid, and tetracosa tetraenoic acid.

2. The method according to claim 1, wherein the adsorbent is one or more selected from the group consisting of a metal silicate, a metal oxide, an activated carbon, a zeolite, an activated clay, and a silica gel.

3. The method according to claim 1, wherein the adsorbent is one or more metal silicates selected from the group consisting of magnesium silicate, calcium silicate, aluminum silicate, sodium silicate, potassium silicate, calcium aluminosilicate, calcium magnesium silicate, and sodium aluminosilicate.

4. The method according to claim 1, wherein the lecithin or lecithin preparation is used for producing an edible oil or fat.

5. The method according to claim 1, wherein the lecithin or lecithin preparation is used for producing a food additive.

6. A method according to claim 1, wherein the lecithin or lecithin preparation is used for producing a cosmetic.

7. A method according to claim 1, wherein the lecithin or lecithin preparation is used for producing a medicine.

8. A method according to claim 1, wherein the lecithin or lecithin preparation is used for producing a feed.

9. A method according to claim 1, wherein the lecithin or lecithin preparation is used for producing an industrial product.

10. A method according to claim 1, wherein the lecithin or lecithin preparation is used for producing a food or drink.

11. A method according to claim 1, wherein the lecithin dispersion in step 1 is non-aqueous.

12. A method according to claim 1, wherein the lecithin dispersion in step 1 has a total phospholipid content and an acid value selected from the group consisting of:

i) a total phospholipid content of 2.5% by mass and an acid value of about 1 or more;

ii) a total phospholipid content of 25% by mass and an acid value of about 10 or more;

iii) a total phospholipid content of 50% by mass and an acid value of about 20 or more; and iv) any respective amounts of total phospholipid content and acid value that provide a ratio of total phospholipid content to acid value of 5× % by mass total phospholipid content to acid value of about 2× or more, wherein the total phospholipid content is between 0.1% and 90%, other than the total phospholipid contents and acid values of i) to iii) above.

* * * * *